(12) United States Patent
Stesin et al.

(10) Patent No.: US 10,453,251 B2
(45) Date of Patent: Oct. 22, 2019

(54) SYSTEMS AND METHODS FOR AUTOMATED MEASUREMENT OF FOOT SIZE USING ELECTRONIC SENSORS

(71) Applicant: Fit-Any, Inc., Woodside, CA (US)

(72) Inventors: Yekaterina Stesin, Woodside, CA (US); Kirill Levichev, Belmont, CA (US); Alex Freed, San Carlos, CA (US)

(73) Assignee: Fit-Any, Inc., Woodside, CA (US)

( * ) Notice: Subject to any disclaimer, the term of this patent is extended or adjusted under 35 U.S.C. 154(b) by 0 days.

(21) Appl. No.: 16/131,047

(22) Filed: Sep. 14, 2018

(65) Prior Publication Data

US 2019/0274395 A1 Sep. 12, 2019

Related U.S. Application Data

(63) Continuation-in-part of application No. 15/373,490, filed on Dec. 9, 2016, now abandoned.

(51) Int. Cl.
| | |
|---|---|
| *G06T 17/00* | (2006.01) |
| *A61B 5/00* | (2006.01) |
| *G01L 1/20* | (2006.01) |
| *A61B 5/107* | (2006.01) |

(52) U.S. Cl.
CPC ............ *G06T 17/00* (2013.01); *A61B 5/1072* (2013.01); *A61B 5/1073* (2013.01); *A61B 5/6829* (2013.01); *G01L 1/205* (2013.01); *A61B 5/0022* (2013.01); *A61B 5/7264* (2013.01); *A61B 2562/0247* (2013.01)

(58) Field of Classification Search
None
See application file for complete search history.

(56) References Cited

U.S. PATENT DOCUMENTS

| | | | | |
|---|---|---|---|---|
| 9,245,180 | B1* | 1/2016 | Hansen | G06K 9/00362 |
| 2006/0016255 | A1* | 1/2006 | Haselhurst | A43B 3/0005 |
| | | | | 73/172 |
| 2007/0204687 | A1* | 9/2007 | Haselhurst | A43B 3/0005 |
| | | | | 73/172 |
| 2011/0055053 | A1* | 3/2011 | Rutschmann | G06Q 10/087 |
| | | | | 705/27.2 |
| 2016/0051009 | A1* | 2/2016 | Kormann | A43B 13/14 |
| | | | | 36/103 |
| 2016/0081435 | A1* | 3/2016 | Marks | A43D 1/027 |
| | | | | 382/154 |
| 2017/0068774 | A1* | 3/2017 | Cluckers | A61B 5/743 |

* cited by examiner

*Primary Examiner* — Robert J Craddock
(74) *Attorney, Agent, or Firm* — TransPacific Law Group; Pavel I. Pogodin, Esq.

(57) ABSTRACT

A computer-implemented method for estimating a size of a foot, the computer-implemented method being performed in connection with a computer system comprising a central processing unit, a plurality of sensors and a memory, the computer-implemented method comprising: receiving foot measurement data from the plurality of sensors; using the received foot measurement data to build a 3D model of the foot; receiving a 3D model of a shoe; performing a positive or negative match of the 3D model of the foot with the 3D model of a shoe; and providing a result of the positive or negative match to a user.

3 Claims, 3 Drawing Sheets

SYSTEMS AND METHODS FOR AUTOMATED MEASUREMENT OF FOOT SIZE USING ELECTRONIC SENSORS

BACKGROUND OF THE INVENTION

Field of the Invention

The disclosed embodiments relate in general to the field of electronic technology and in particular to a system and method for shoe fitting and particularly to determining the size and shape of the foot using electronic sensors.

Description of the Related Art

As would be appreciated by persons of ordinary skill in the art, shoe fitting has been historically manual and tedious process. The method currently in use to match a shoe to a particular foot involves mechanically measuring the foot's length and sometimes the width and instep, and then choosing the specific size of a particular shoe make and model that is the best match for the taken measurements. The choosing of the specific size of the shoe is not precise and often requires trying on several different shoes even when the length, width, and instep of the foot are known, because both the foot and the shoe are complex three-dimensional objects and one to three measurements often provide insufficient information to make the foot-shoe matching decision without actually trying on the shoe. Another problem in matching shoe to a foot using the conventional technology is that taking mechanical measurements of the foot often introduces measurement errors.

Thus, in view of the foregoing deficiencies of the conventional technology, it would be desirable to have a system and method for automated shoe fitting and particularly for determining the size and shape of the foot using electronic sensors.

SUMMARY OF THE INVENTION

The inventive methodology is directed to methods and systems that substantially obviate one or more of the above and other problems associated with conventional technology.

In accordance with one aspect of the embodiments described herein, there is provided a footwear matching system, said system comprising: a mobile foot scanning slip-in with a plurality of sensors to yield a plurality of user foot data coupled to a memory element with instructions, which, when executed in connection with a processing unit, cause the footwear matching system to match available footwear by: receiving user foot data comprising a plurality of sensed data and user inputted data; rendering a 3-D representation of the user foot based on the user foot data; referencing said user foot 3-D representation against a learned table of footwear data, wherein the footwear data is at least one of a statistical aggregation across at least one of a brand line, size line, style line, outer composition line, inner-composition line, color-way line, or footwear 3-D representation line; and pushing a list of at least two footwear with a ranked threshold-grade match of user foot 3-D representation with statistical aggregation across at least one line for any given matched footwear.

In accordance with another aspect of the embodiments described herein, there is provided a footwear matching system, said system comprising: a mobile foot scanning slip-in with a plurality of sensors to yield a plurality of user foot data coupled to a memory element with instructions, which, when executed in connection with a processing unit, cause the footwear matching system to match available footwear by: receiving user foot data comprising a plurality of sensed data and user inputted data by a receiving module; rendering a 3-D representation of the user foot based on the user foot data by a rendering module; referencing said user foot 3-D representation against a learned table of footwear data by a matching module, wherein the footwear data is at least one of a statistical aggregation across at least one of a brand line, size, line, style line, outer composition line, inner-composition line, color-way line, or footwear 3-D representation line; pushing a list of at least two footwear with a ranked threshold-grade match of user foot 3-D representation with statistical aggregation across at least one line for any given matched footwear; and wherein the list of footwear is from a curated native inventory of footwear.

In accordance with another aspect of the embodiments described herein, there is provided a footwear matching system, said system comprising: a mobile foot scanning slip-in with a plurality of sensors to yield a plurality of user foot data coupled to a memory element with instructions, which, when executed in connection with a processing unit, cause the footwear matching system to match available footwear by: receiving user foot data comprising a plurality of sensed data and user inputted data; rendering a 3-D representation of the user foot based on the user foot data; referencing said user foot 3-D representation against a learned table of footwear data, wherein the footwear data is at least one of a statistical aggregation across at least one of a brand line, size line, style line, outer composition line, inner-composition line, color-way line, or footwear 3-D representation line; and pushing a list of at least two footwear with a ranked threshold-grade match of user foot 3-D representation with statistical aggregation across at least one line for any given matched footwear; and wherein the list of footwear is from at least one of a curated native inventory or third-party sourced inventory.

In accordance with another aspect of the embodiments described herein, there is provided a footwear matching system, said system comprising: a mobile foot scanning slip-in with a plurality of sensors to yield a plurality of user foot data coupled to a memory element with instructions, which, when executed in connection with a processing unit, cause the footwear matching system to match available footwear by: receiving user foot data comprising a plurality of sensed data and user inputted data; rendering a 3-D representation of the user foot based on the user foot data; referencing said user foot 3-D representation against a learned table of footwear data, wherein the footwear data is at least one of a statistical aggregation across at least one of a brand line, size line, style line, outer composition line, inner-composition line, color-way line, or footwear 3-D representation line, source line, or price line; pushing a list of at least two footwear with a ranked threshold-grade match of user foot 3-D representation with statistical aggregation across at least one line for any given matched footwear; and wherein the list of footwear is from at least one of a curated native inventory or third-party sourced inventory.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify the embodiments of the present invention and, together with the description, serve to explain and illustrate principles of the inventive technique. Specifically.

DETAILED DESCRIPTION

Figure 1:
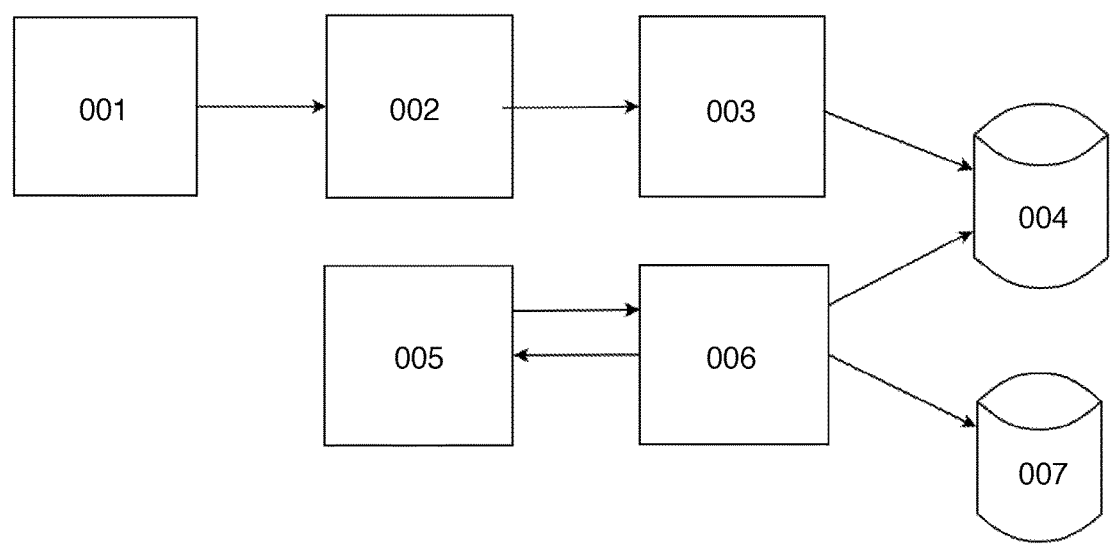
FIG. 1 illustrates an exemplary embodiment of a logical diagram of an embodiment of the system for automatic measurement of foot dimensions and shapes.

In the following detailed description, reference will be made to the accompanying drawing(s), in which identical functional elements are designated with like numerals. The aforementioned accompanying drawings show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of a software running on a general purpose computer, in the form of a specialized hardware, or a combination of software and hardware.

One or more embodiments described herein solve the above-mentioned and other shortcomings of the prior art technology by:

(1) electronically measuring multiple foot dimensions (including but not limited to length, width, heel width, instep, ball to heel length) thus excluding human error that may be introduced during the manual measurements; and (2) building a three-dimensional model of the foot which is then matched to a three-dimensional model of the shoe with much greater precision that could be accomplished using the conventional manual measurements.

In one or more embodiments, the inventive system for automatic measurement of foot dimensions and shapes incorporates a plurality of sensors including, but not limited to, inductive sensors, infrared sensors, visible spectrum sensors (photo cameras) and/or pressure sensors. In one or more embodiments, the aforesaid plurality of sensors are mechanically attached to a platform and are configured to measure multiple parameters of the foot placed onto the aforesaid platform. The list of the parameters that could be measured using the described embodiment of the system include, without limitation, the overall length, arch length, width, heel width, and instep. As would be appreciated by persons of ordinary skill in the art, the above list of measured parameters should not be construed in a limiting sense and may other parameters of the foot may be similarly measured.

In one or more embodiments, the described system for automatic measurement of foot dimensions and shapes further incorporates a CPU and the corresponding firmware that collectively are capable of gathering the information from the above-described multiple sensors and transferring the collected information (e.g. foot measurements) as well as a unique identifier (e.g. a serial number) to a software application executing on a general purpose computer or a mobile computing device. The aforesaid transfer of the foot measurement data to the software application may be accomplished by any known means of data transfer, including, without limitation, USB interconnect, LAN, WIFI, Bluetooth or any now known or later developed data transfer interconnect or protocol.

In one or more embodiments, the described system for automatic measurement of foot dimensions and shapes further incorporates an application executing on the computer, which could be (but is not limited to) a smartphone, a tablet, a personal computer, or a kiosk. This application receives the foot measurement data from the above-described sensors as well as the serial number of the corresponding device. In one or more embodiments, the foot measurement data is stored locally. In one embodiment, the system optionally enables the user to input user's personal information. The aforesaid application communicates with a backend server via the Internet and transmits the collected foot measurement data and identification (user personal data, device serial number or both) to a server.

In one or more embodiments, the described system for automatic measurement of foot dimensions and shapes further incorporates a backend software (server) that implements an application-level Internet protocol that enables the receipt of the foot measurement data and matches the foot measurements to a particular user. The server may further store the received foot measurement data in a database, retrieve the foot measurement data for a particular user or users, and perform statistical computations on the received dataset. In various embodiments, the aforesaid database may be implemented based on any now known or later developed type of database management system, such as a relational database management system, including, without limitation, MySQL, Oracle, SQL Server, DB2, SQL Anywhere, PostgreSQL, SQLite, Firebird, redis, MongoDB, Hadoop and/or MaxDB, which are well-known to persons of skill in the art. In an alternative embodiment, a cloud-based distributed database, such as Amazon Relational Database (Amazon RDS), well known to persons of ordinary skill in the art, may also be used.

In one or more embodiments, the described system for automatic measurement of foot dimensions and shapes further incorporates a backend software (server) that implements application-level Internet protocol that enables it to receive a 3D model dataset for a particular make, model and size of the shoe, to build a 3D model of a foot using the received set of the measurements and to perform positive or negative match of the 3D model of the foot with the 3D model of a shoe. The aforesaid server may further store the results of the matching in the aforesaid database and transmit those results to a user computer (via browser). Additionally, the aforesaid server may be configured to perform various statistical computations on the dataset and transmit those computations to the user computer (e.g. via browser).

FIG. 1 illustrates an exemplary embodiment of a logical diagram of an embodiment of the system for automatic measurement of foot dimensions and shapes.

Element 001 of FIG. 1 is the foot measuring device. In various embodiments, it incorporates (a) plurality of distance measuring sensors of the types that include, but are not limited to, inductive sensors, photo cameras, infrared sensors, ultrasound sensors and (b) an electronic board with the CPU and the non-volatile memory containing the corresponding firmware that collects the sensors outputs, has a unique identifiable information (serial number), maintains a communication channel with a computer application 002 through the USB interconnect, Ethernet, LAN, WIFI, Bluetooth or using any other now known or later developed interconnect or data transfer protocol.

Element 002 of FIG. 1 is the client application. It resides on the user computer (smartphone, tablet, personal computer or kiosk), maintains a communication channel with the single measuring device 001 and with a server 003. Optionally, the client application 002 may enable inputting the user identification information that would be transmitted to the server 003.

Element 003 of FIG. 1 is the measuring server. In one embodiment, it maintains a data connection with multiple client applications 002. The measuring server 003 receives the foot measurement data from each instance of the client application 002 with the user-identifying information and stores this information in the database 004.

Element 004 of FIG. 1 is the measurements database. It stores the foot measurement data collected as described above from measuring users' feet and transmits this stored data back in response to an appropriate query.

Element 005 of FIG. 1 is the matching client (browser). It communicates with the matching server 006, permits the user to upload a file containing a 3D model of a particular make, model and size of the shoe to the matching server 006, allows the user to request the matching of a particular user's foot with a particular shoe and displays the result of the matching.

Element 006 of FIG. 1 is the matching web server. It creates a 3D model of a foot using the foot measurements data stored in the database 004, stores a 3D model of a shoe uploaded from the client browser 005 in the database 007, performs matching between the 3D model of a foot and the 3D model of a shoe, stores the results of the matching (such as "no match," "specific show size," etc.) in the database 007, transmits the result of the matching to the browser 005, and also handles other queries initiated from the browser 005 to the database 007 and the database 004. Those queries may include but are not limited to "what measurements a particular user has?", "when the measurement was made?" or "on what device?" The matching web server 007 may further aggregate statistics over full set of users or a particular subset of users.

Element 007 of FIG. 1 is the shoes database. It sores the data describing a 3D model of a particular make, model and size of shoe and transmits the aforesaid 3D model data back, in response to a query.

In one or more embodiments, the described system for automatic measurement of foot dimensions and shapes utilizes a pressure sensor. In one or more embodiments of the aforesaid system, a plurality of the aforesaid pressure sensors placed in the insole are used to determine the foot's length, arch form, degree of flatness, degree of over- or under-pronation. These pressure sensors, are designed with a use of a conductive foam, including but not limited to, rubber impregnated with graphite particles, which has the ability to change resistance under pressure. This foam is placed on top of a printed circuit board (PCB) containing a plurality of the sensors, each sensor including a contact pair printed on the PCB. The pressure from the foot varies in different locations and thus compresses the foam differently.

As would be appreciated by persons of ordinary skill in the art, more compressed foam has less resistance and thus the voltage drop is less across a contact pair that is in the vicinity of the area with greater pressure applied. By reading the voltage of each contact pair it is thus possible to create a 2-dimensional pressure map of the foot.

Figure 2:
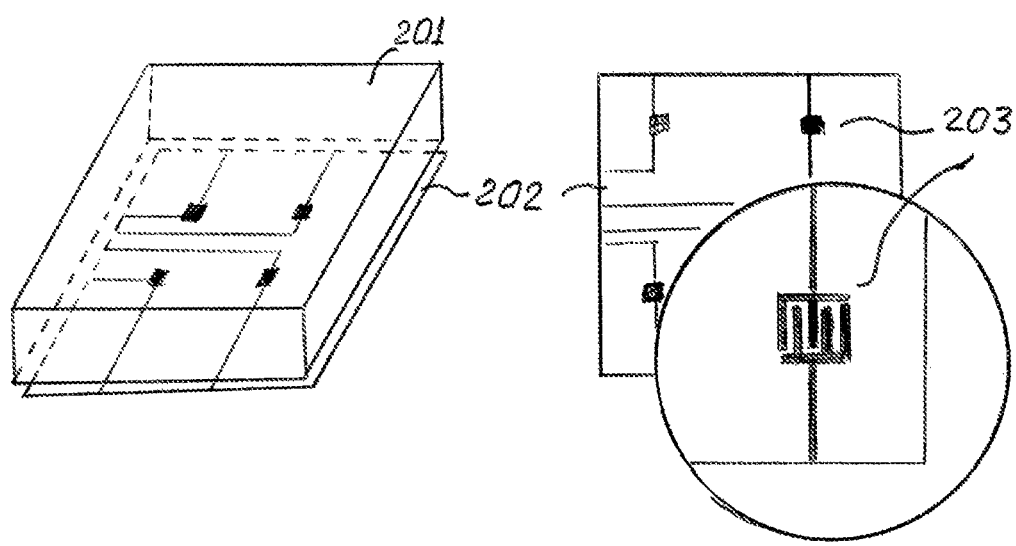
FIG. 2 is a diagram of an exemplary embodiment of a pressure sensor.

FIG. 2 is a diagram of an exemplary embodiment of a pressure sensor.

Element 201 of FIG. 2 is the conductive foam insole. It is placed on top of PCB (201) and pressure (204) applied by the foot compresses the foam.

Element 202 of FIG. 2 is the Printed Circuit Board (PCB). It contains plurality of contact pairs and electronics for measuring the voltage drop across each contact pair.

Element 203 of FIG. 2 is a contact pair. It incorporates a pair of metal conductors printed on the surface of PCB (202) in a manner that facilitates better contact with the conductive foam (201).

As would be appreciated by persons of ordinary skill in the art, previously described implementations used measurements based 3D models to predict a match between feet and shoes. The problem with those implementations is that shoes are flexible and the inner shape of a shoe at rest being a close match to a 3D model of a given foot does not guaranty that it will be comfortable in real life.

Therefore, one embodiment is using the foot measurements not as a final criterion for matching with a brand/size combination, but as a part of a hardware plus software apparatus and method of predicting good matches. An embodiment of the described system operated in accordance with the following algorithm:

1. A person takes measurements that are sent to a cloud based processing systems with a database. In addition the same person provides information of other brands of shoes with particular sizes that are a good match. Based on this the algorithm makes the first suggestion of a possible match.

2. The person tries the suggested pair of shoes and provides feedback to the system on whether the shoes fit well or not and if not in what way.

3. This information is used to improve the further predictions for not just this person, but for any new customer who's measurements are close to previous customers.

4. The algorithm is a form of machine learning system that accumulates more and more data and improves predictions as more data points become available.

Furthermore, an embodiment of the system includes software that can receive and persist the measurements of the foot for a particular user, and receive and persist that user's fit rating for a particular shoe make, model, and size.

Furthermore, in one or more embodiments, the system consists of the Artificial Neural Network (ANN) software that is able to train itself on the feet measurements and the corresponding human fit ratings, and, once trained, is able to predict the fit of the particular shoe make, model, and size to a particular foot that was hitherto unknown.

Alternatively, an implementation can use a "random forest" algorithm to determine which measured data points are the best predictors of a good fit based on the accumulated statistical data and feedback from the users that actually tried on recommended footwear.

Figure 3:
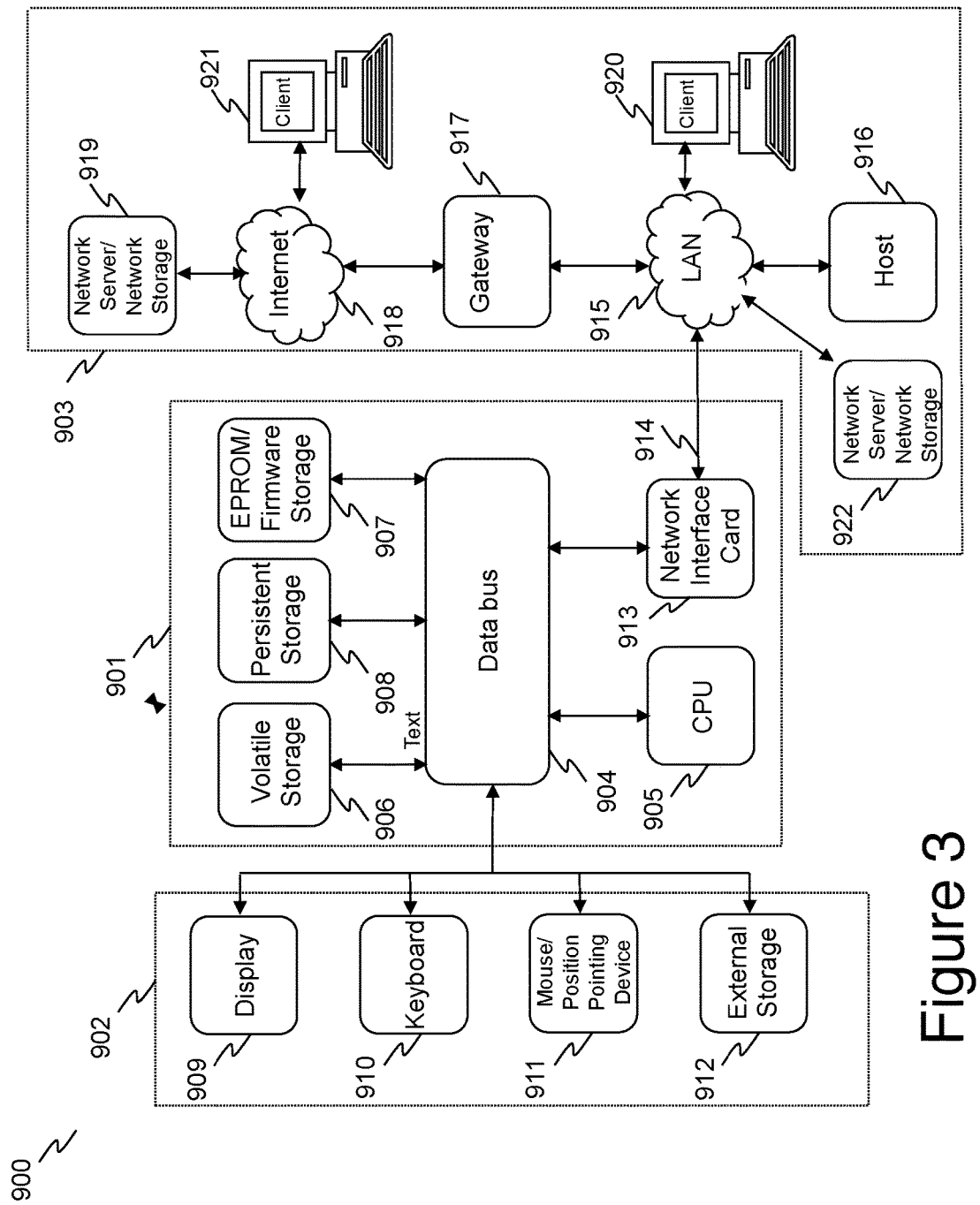
FIG. 3 illustrates an exemplary embodiment of a server platform upon which the described embodiments may be implemented.

FIG. 3 illustrates an exemplary embodiment of a computer platform upon which the inventive system may be implemented. Specifically, FIG. 3 represents a block diagram that illustrates an embodiment of a computer/server system 900 upon which an embodiment of the inventive methodology may be implemented. The system 900 includes a computer/server platform 901, peripheral devices 902 and network resources 903.

In one or more embodiments, the computer platform 901 may include a data bus 904 or other communication mechanism for communicating information across and among various parts of the computer platform 901, and a processor 905 coupled with bus 904 for processing information and performing other computational and control tasks. Computer platform 901 also includes a volatile storage 906, such as a random access memory (RAM) or other dynamic storage device, coupled to bus 904 for storing various information as well as instructions to be executed by processor 905. The volatile storage 906 also may be used for storing temporary variables or other intermediate information during execution of instructions by processor 905. Computer platform 901 may further include a read only memory (ROM or EPROM) 907 or other static storage device coupled to bus 904 for storing static information and instructions for processor 905, such as basic input-output system (BIOS), as well as various system configuration parameters. A persistent storage device 908, such as a magnetic disk, optical disk, or solid-state flash memory device is provided and coupled to bus 904 for storing information and instructions.

Computer platform 901 may be coupled via bus 904 to a display 909, such as a cathode ray tube (CRT), plasma display, or a liquid crystal display (LCD), for displaying information to a system administrator or user of the computer platform 901. An input device 910, including alphanumeric and other keys, is coupled to bus 904 for communicating information and command selections to processor 905. Another type of user input device is cursor control device 911, such as a mouse, a trackball, or cursor direction keys for communicating direction information and command selections to processor 905 and for controlling cursor movement on display 909. This input device typically has two degrees of freedom in two axes, a first axis (e.g., x) and a second axis (e.g., y), that allows the device to specify positions in a plane.

An external storage device 912 may be coupled to the computer platform 901 via bus 904 to provide an extra or removable storage capacity for the computer platform 901. In an embodiment of the computer system 900, the external removable storage device 912 may be used to facilitate exchange of data with other computer systems.

The invention is related to the use of computer system 900 for implementing the techniques described herein. In an embodiment, the inventive system may reside on a machine such as computer platform 901. According to one embodiment of the invention, the techniques described herein are performed by computer system 900 in response to processor 905 executing one or more sequences of one or more instructions contained in the volatile memory 906. Such instructions may be read into volatile memory 906 from another computer-readable medium, such as persistent storage device 908. Execution of the sequences of instructions contained in the volatile memory 906 causes processor 905 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 905 for execution. The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks, such as storage device 908. Volatile media includes dynamic memory, such as volatile storage 906.

Common forms of computer-readable media include, for example, a floppy disk, a flexible disk, hard disk, magnetic tape, or any other magnetic medium, a CDROM, any other optical medium, punchcards, papertape, any other physical medium with patterns of holes, a RAM, a PROM, an EPROM, a FLASH-EPROM, a flash drive, a memory card, any other memory chip or cartridge, or any other medium from which a computer can read.

Various forms of computer readable media may be involved in carrying one or more sequences of one or more instructions to processor 905 for execution. For example, the instructions may initially be carried on a magnetic disk from a remote computer. Alternatively, a remote computer can load the instructions into its dynamic memory and send the instructions over a telephone line using a modem. A modem local to computer system can receive the data on the telephone line and use an infrared transmitter to convert the data to an infra-red signal. An infra-red detector can receive the data carried in the infra-red signal and appropriate circuitry can place the data on the data bus 904. The bus 904 carries the data to the volatile storage 906, from which processor 905 retrieves and executes the instructions. The instructions received by the volatile memory 906 may optionally be stored on persistent storage device 908 either before or after execution by processor 905. The instructions may also be downloaded into the computer platform 901 via Internet using a variety of network data communication protocols well known in the art.

The computer platform 901 also includes a communication interface, such as network interface card 913 coupled to the data bus 904. Communication interface 913 provides a two-way data communication coupling to a network link 915 that is coupled to a local network 915. For example, communication interface 913 may be an integrated services digital network (ISDN) card or a modem to provide a data communication connection to a corresponding type of telephone line. As another example, communication interface 913 may be a local area network interface card (LAN NIC) to provide a data communication connection to a compatible LAN. Wireless links, such as well-known 802.11a, 802.11b, 802.11g and Bluetooth may also be used for network implementation. In any such implementation, communication interface 913 sends and receives electrical, electromagnetic or optical signals that carry digital data streams representing various types of information.

Network link 914 typically provides data communication through one or more networks to other network resources. For example, network link 914 may provide a connection through local network 915 to a host computer 916, or a network storage/server 917. Additionally or alternatively, the network link 914 may connect through gateway/firewall 917 to the wide-area or global network 918, such as an Internet. Thus, the computer platform 901 can access network resources located anywhere on the Internet 918, such as a remote network storage/server 919. On the other hand, the computer platform 901 may also be accessed by clients located anywhere on the local area network 915 and/or the Internet 918. The network clients 920 and 921 may themselves be implemented based on the computer platform similar to the platform 901.

Local network 915 and the Internet 918 both use electrical, electromagnetic or optical signals that carry digital data streams. The signals through the various networks and the signals on network link 915 and through communication interface 913, which carry the digital data to and from computer platform 901, are exemplary forms of carrier waves transporting the information.

Computer platform 901 can send messages and receive data, including program code, through the variety of network(s) including Internet 918 and LAN 915, network link 915 and communication interface 913. In the Internet example, when the system 901 acts as a network server, it might transmit a requested code or data for an application program running on client(s) 920 and/or 921 through Internet 918, gateway/firewall 917, local area network 915 and communication interface 913. Similarly, it may receive code from other network resources.

The received code may be executed by processor 905 as it is received, and/or stored in persistent or volatile storage devices 908 and 906, respectively, or other non-volatile storage for later execution.

It should be understood that processes and techniques described herein are not inherently related to any particular apparatus and may be implemented by any suitable combination of software components. Further, various types of general purpose software components may be used in accordance with the teachings described herein. It may also prove advantageous to extend the taxonomy as well as number of media Channels and Channel Actions to perform the method steps described herein. The present invention has been described in relation to particular examples, which are intended in all respects to be illustrative rather than restrict. Those skilled in the art will appreciate that many different combinations of software components, and software services will be suitable for practicing the present invention. For example, the described software may be implemented in a wide variety of programming or scripting languages, such as .NET, PHP, Java, etc.

Moreover, other implementations of the invention will be apparent to those skilled in the art from consideration of the specification and practice of the invention disclosed herein. Various aspects and/or components of the described embodiments may be used singly or in any combination in the computerized systems and computer-implemented methods for automated foot size and shape measurement. It is intended that the specification and examples be considered as exemplary only, with a true scope and spirit of the invention being indicated by the following claims.

What is claimed is:

1. A footwear matching system, said system comprising:
a mobile foot scanning slip-in with a plurality of sensors to yield a plurality of user foot data coupled to;
a memory element with instructions, which, when executed in connection with a processing unit, cause the footwear matching system to match available footwear by:
receiving user foot data comprising a plurality of sensed data and user inputted data;
rendering a 3-D representation of the user foot based on the user foot data;
referencing said user foot 3-D representation against a learned table of footwear data, wherein the footwear data is at least one of a statistical aggregation across at least one of a brand line, size line, style line, outer composition line, inner-composition line, color-way line, or footwear 3-D representation line; and
pushing a list of at least two footwear with a ranked threshold-grade match of user foot 3-D representation with statistical aggregation across at least one line for any given matched footwear.

2. A footwear matching system, said system comprising:
a mobile foot scanning slip-in with a plurality of sensors to yield a plurality of user foot data coupled to;
a memory element with instructions, which, when executed in connection with a processing unit, cause the footwear matching system to match available footwear by:
receiving user foot data comprising a plurality of sensed data and user inputted data by a receiving module;
rendering a 3-D representation of the user foot based on the user foot data by a rendering module;
referencing said user foot 3-D representation against a learned table of footwear data by a matching module, wherein the footwear data is at least one of a statistical aggregation across at least one of a brand line, size, line, style line, outer composition line, inner-composition line, color-way line, or footwear 3-D representation line;
pushing a list of at least two footwear with a ranked threshold-grade match of user foot 3-D representation with statistical aggregation across at least one line for any given matched footwear; and wherein the list of footwear is from a curated native inventory of footwear.

3. A footwear matching system, said system comprising:
a mobile foot scanning slip-in with a plurality of sensors to yield a plurality of user foot data coupled to;
a memory element with instructions, which, when executed in connection with a processing unit, cause the footwear matching system to match available footwear by:
receiving user foot data comprising a plurality of sensed data and user inputted data;
rendering a 3-D representation of the user foot based on the user foot data;
referencing said user foot 3-D representation against a learned table of footwear data, wherein the footwear data is at least one of a statistical aggregation across at least one of a brand line, size line, style line, outer composition line, inner-composition line, color-way line, or footwear 3-D representation line; and
pushing a list of at least two footwear with a ranked threshold-grade match of user foot 3-D representation with statistical aggregation across at least one line for any given matched footwear; and wherein the list of footwear is from at least one of a curated native inventory or third-party sourced inventory.

* * * * *